United States Patent
Hapiot et al.

(10) Patent No.: US 10,315,983 B2
(45) Date of Patent: Jun. 11, 2019

(54) FATTY AMINO ALCOHOLS AND PROCESS FOR PREPARING SAME

(71) Applicants: PIVERT S.A.S., Venette (FR); CENTRE NATIONAL DE LA RECHERCHE SCIENTIFIQUE (CNRS), Paris (FR); UNIVERSITE D'ARTOIS, Arras (FR)

(72) Inventors: Frederic Hapiot, Ennevelin (FR); Eric Monflier, La Madeleine (FR); Theodore Vanbesien, Lille (FR)

(73) Assignees: PIVERT S.A.S., Venette (FR); CENTRE NATIONAL DE LA RECHERCHE SCIENTIFIQUE (CNRS), Paris (FR); UNIVERSITE D'ARTOIS, Arras (FR)

( * ) Notice: Subject to any disclaimer, the term of this patent is extended or adjusted under 35 U.S.C. 154(b) by 11 days.

(21) Appl. No.: 15/541,769

(22) PCT Filed: Feb. 9, 2016

(86) PCT No.: PCT/EP2016/052712
§ 371 (c)(1),
(2) Date: Jul. 6, 2017

(87) PCT Pub. No.: WO2016/128390
PCT Pub. Date: Aug. 18, 2016

(65) Prior Publication Data
US 2018/0002274 A1 Jan. 4, 2018

(30) Foreign Application Priority Data
Feb. 12, 2015 (FR) ...................................... 15 00276

(51) Int. Cl.
C07C 229/12 (2006.01)
C07C 227/10 (2006.01)

(52) U.S. Cl.
CPC .......... C07C 229/12 (2013.01); C07C 227/10 (2013.01)

(58) Field of Classification Search
CPC ...... C07C 229/12; C07C 227/10; C07C 33/30
See application file for complete search history.

(56) References Cited

U.S. PATENT DOCUMENTS 3,513,200 A 5/1970 Biale
7,220,884 B2 * 5/2007 Briggs .................... C07C 33/30
544/178

FOREIGN PATENT DOCUMENTS

DE 10321421 A1 12/2004

OTHER PUBLICATIONS

Zhao, H.P. et a., Syntheses and properties of cross-linked polymers from functionalized triglycerides, 2008, Journal of Applied Polymer Science, vol. 110, issue 2, pp. 647-656 (Year: 2008).*

(Continued)

*Primary Examiner* — Yate' K Cutliff
(74) *Attorney, Agent, or Firm* — Avery N. Goldstein; Blue Filament Law PLLC (57) ABSTRACT

The present invention relates to amino alcohol compounds and to the preparation thereof from fatty esters comprising at least two carbon-carbon double bonds. In particular, the present invention relates to fatty amino alcohol compounds obtained by means of a process coupling, in a single step, a hydroaminomethylation reaction and a hydrohydroxymethylation reaction.

8 Claims, 2 Drawing Sheets

(56) References Cited

OTHER PUBLICATIONS

Dorwald, F.Z., Side reaction inorganic synthesis, 2005 Wiley-VCH, Chapter 1, pp. 1-16 (Year: 2005).*

Reppe, W. and Vetter, H., "Carbonylation VI. Synthesis with metal carbonyls", Justus Liebigs Ann Chem (1953), pp. 133-161, vol. 582, doi:10.1002/jlac.19535820107.

Behr, A. et al., "Hydroaminomethylation of fatty acids with primary and secondary amines—A new route to interesting surfactant substrates", Eur. J. Lipid Sci. Technol. (2000), pp. 467-471, vol. 102, Copyright Wiley-VCH Verlag GmbH, 69451 Weinheim (2000).

Wang, Y.Y. et al., "The catalytic hydroaminomethylation of long chain alkenes with dimethylamine in aqueous-organic two-phase system", Applied Catalysis A: General (Available online: Jul. 2, 2004), pp. 151-155, vol. 272, Copyright Elsevier B.V. (2004); www.sciencedirect.com.

Müller, K.S. et al., "Synthesis of polyamines via hydroaminomethylation of alkenes with urea—a new, effective and versatile route to dendrons and dendritic core molecules", Organic & Biomolecular Chemistry (Published online: Jan. 9, 2006), pp. 826-835, vol. 4, Copyright the Royal Society of Chemistry (2006); http://pubs.rsc.org.

Behr, A. and Westfechtel, A., "Catalytic processes in the production of valuable natural oils and fats", Chemie Ingenieur Technik (2007), pp. 621-636, vol. 79, issue 5, Copyright Wiley-VCH Verlag GmbH & Co. KGaA, Weinheim (2007); www.cit-journal.de.

Zhao, H.P. et al., "Syntheses and Properties of Cross-Linked Polymers From Functionalized Triglycerides", Journal of Applied Polymer Science (Published online: Jul. 9, 2008), pp. 647-656, vol. 110, issue 2, Copyright Wiley Periodicals, Inc. (2008); www.interscience.wiley.com.

Behr, A. et al., "A highly efficient method for the hydroaminomethylation of long-chain alkenes under aqueous, piphasic conditions", Tetrahedron Letters (Available online: Mar. 1, 2010), pp. 2438-2441, vol. 51, Copyright Elsevier Ltd. (2010); www.elsevier.com/locate/tetlet.

Behr, A. et al., "Diester monomers from methyl oleate and proline via tandem hydroaminomethylation-esterification sequence with homogeneous catalyst recycling using TMS-technique", Eur. J. Lipid Sci. Technol. (2014), pp. 477-485, vol. 116, Copyright Wiley-VCH Verlag GmbH & Co. KGaA, Weinheim (2014); www.ejlst.com.

International Search Report dated Mar. 21, 2016 for International Application No. PCT/EP2016/052712 filed Feb. 9, 2016.

* cited by examiner

FATTY AMINO ALCOHOLS AND PROCESS FOR PREPARING SAME

FIELD OF THE INVENTION

The invention relates to fatty amino alcohols and to the process for preparing them, preferably fatty amino alcohol of mono-, di-, or triglycerides. The invention pertains more particularly to a process for preparing fatty amino alcohol from fatty esters comprising at least two carbon-carbon double bonds.

TECHNOLOGICAL BACKGROUND OF THE INVENTION

Aliphatic amines are commonly employed for the synthesis of products or intermediates which are used in the pharmaceutical or agrochemical industries. Amines of this type are also used as precursors for the production of polymer such as polyurethanes.

The hydroaminomethylation reaction was reported by Reppe (Liebigs Ann. Chem. 1953, 582, 133-161), using a cobalt catalyst. This reaction comprises a one-pot tandem hydroformylation/amination reaction of an olefin, in which the aldehyde from the hydroformylation of the olefin reacts with a primary or secondary amine to form a secondary or tertiary amine, respectively.

U.S. Pat. No. 3,513,200 describes the hydroaminomethylation of an olefin in the presence of a rhodium/PPh$_3$ catalyst for the synthesis of tertiary amines. Hydroaminomethylation reactions are also known from DE 10321421, U.S. Pat. No. 7,220,884 or Behr et al. (Tetrahedron Letters 51 (2010) 2438-2441). To improve the performance parameters of the reaction, the use of cocatalysts, especially based on rhodium and on iridium, allows rapid formation of amine. The rhodium intervenes in the hydroformylation reaction, the iridium in the catalytic reduction of the intermediate imine or enamine. Hydroaminomethylation reactions are also known in which polymer is obtained directly. Müller et al. showed that the use of polyfunctional substrate or polyfunctional amine allows the preparation of polyamine dendrimers by hydroaminomethylation (Müller et al., Org. Biomol. Chem., 2006, 4, 826-835).

Wang et al. showed the efficacy of hydroaminomethylation reactions on fatty olefins in the presence of various amines (Wang et al. Applied Catalysis A: General 272 (2004) 151-155). The reactions were carried out in emulsion, and required the use of surfactants such as CTAB, entailing additional steps for recovery of the substrate and the catalyst. Behr et al. used the methyl esters of oleic acid in hydroaminomethylation reactions in which the amine used is, for example, proline (Eur. J. Lipid Sci. Technol. 2014, 116, 477-485; Eur. J. Lipid Sci. Technol. 102 (2000) 467-471). This type of reaction exclusively only forms amines from monounsaturated fatty olefins. The hydroaminomethylation of oleyl alcohol is also known from Behr et al., Chemie Ingenieur Technik, 2007, 79, 5, 621-636.

SUMMARY OF THE INVENTION

The present invention allows amino alcohol compounds, these being compounds comprising at least one functional alcohol moiety and at least one functional amine moiety, to be prepared from polyunsaturated compounds. The process is of particular interest for the selective preparation of amino alcohol compounds from polyunsaturated esters, preferably polyunsaturated fatty esters. The process according to the present invention combines, in a single step, a hydroaminomethylation reaction of a first carbon-carbon double bond and a hydrohydroxymethylation reaction, namely a hydrogenation reaction of aldehydes formed in-situ by hydroformylation of a second carbon-carbon double bond.

According to a first aspect of the present invention, amino alcohol compounds are provided. Said compounds are of formula $R^5$—$[C(R^1)(R^2)]_u$—$R^6$ (Ia) in which u is an integer between 1 and 10;

$R^1$, $R^2$, $R^5$, and $R^6$ independently for each of the units $[C(R^1)(R^2)]_u$, and independently of one another represent H, —$OR^{15}$, —$OC(O)R^{15}$, $C_1$-$C_{30}$ alkyl unsubstituted or substituted by one or more groups $OR^{15}$, $C_6$-$C_{12}$ aryl unsubstituted or substituted by one or more groups —$OR^{15}$, $C_3$-$C_{10}$ cycloalkyl unsubstituted or substituted by one or more groups —$OR^{15}$, a group of formula (II), or $R^6$ or $R^5$ and $R^1$ of any one of the units $[C(R^1)(R^2)]_u$, or $R^1$ of any one of the units $[C(R^1)(R^2)]_u$ and $R^2$ of any one of the units $[C(R^1)(R^2)]_u$, form, together with the carbon atoms to which they are attached, a 5- or 6-membered heterocycle, where the group of formula (II)

(II)

comprises at least 4 carbon atoms and at most 80 carbon atoms, and in which n is an integer between 1 and 15, advantageously between 1 and 10, preferably between 1 and 6, more particularly between 1 and 5;

A independently for each of the units [A]$_n$ is a group of formula —[(X)$_a$—Y—(X)$_b$]— in which Y is C(R)=C(R'), C(R)(CH$_2$NR$^3$R$^4$)—CH(R'), C(R)(CH$_2$OH)—CH(R') or C(R)(R');

X independently for each of the units (X)$_a$ and (X)$_b$ and independently for each of the units [A]$_n$ represents a $C_1$-$C_{10}$ alkyl, $C_6$-$C_{18}$ aryl, $C_3$-$C_{10}$ cycloalkyl, five- to seven-membered heterocycle, five- to seven-membered heteroaryl, or a group of formula —[(C(R")(R'''))$_c$—(Z)—(C(R")(R'''))$_d$]— in which Z is $C_6$-$C_{18}$ aryl, $C_3$-$C_{10}$ cycloalkyl, five- to seven-membered heterocycle or five- to seven-membered heteroaryl;

R, R', R" and R''' independently of one another, independently for each of the units (C(R")(R''')), and independently for each of the units Y represent H, $C_1$-$C_{10}$ alkyl, $C_6$-$C_{12}$ aryl or $C_3$-$C_{10}$ cycloalkyl;

$R^3$ and $R^4$ independently of one another represent H, $C_1$-$C_{10}$ alkyl, $C_6$-$C_{12}$ aryl, benzyl, $C_3$-$C_{10}$ cycloalkyl, or $R^3$ and $R^4$ together with the nitrogen atom to which they are attached form a five- or six-membered heterocycle;

where a, b, c, and d are integers between 0 and 20, advantageously between 0 and 15, preferably between 0 and 10, the sum of a+b or c+d being less than 20;

$R^{15}$ represents H, $C_1$-$C_{30}$ alkyl unsubstituted or substituted by one or more OH groups or by one or more groups of formula (II) as defined above, or five- or six-membered heterocycle unsubstituted or substituted by one or more —OH groups or by one or more groups of formula (II) as defined above;

the compound of formula (Ia) comprising at least one group of formula (II) in which Y is CR(CH$_2$NR$^3$R$^4$)—CHR' in at least one of the units [A]$_n$, and at least one group of formula (II) in which Y is CR(CH$_2$OH)—CHR in at least one of the units [A]$_n$.

Provided according to a second aspect of the present invention is a process for preparing amino alcohol from polyunsaturated compounds. The present invention more particularly provides a process for preparing amino alcohol from a compound B comprising at least two carbon-carbon double bonds, said process comprising a step a) of combining, with stirring, at least one precatalyst, an amine of formula HNR$^3$R$^4$ in which R$^3$ and R$^4$ independently of one another represent H, C$_1$-C$_{10}$ alkyl, C$_6$-C$_{12}$ aryl, C$_3$-C$_{10}$ cycloalkyl, or R$^3$ and R$^4$ together with the nitrogen atom to which they are attached form a five- or six-membered heterocycle; and said compound B, under an atmosphere of hydrogen and carbon monoxide. Said precatalyst is a complex of transition metals selected from columns 8 to 10 of the periodic table.

The present invention allows, surprisingly, the selective preparation of fatty amino alcohol compounds from a polyunsaturated compound. The present invention more particularly allows the selective preparation of fatty ester compounds, such as triglycerides, comprising one functional moiety of amine type and two functional moieties of alcohol type, or the selective preparation of fatty ester compounds, such as triglycerides, comprising two functional moieties of amine type and one functional moiety of alcohol type.

DETAILED DESCRIPTION OF THE PRESENT INVENTION

The term "substituted" as used in the present invention signifies that one or more hydrogen atoms of the moiety to which the term "substituted" refers is replaced by one of the substituents named, on condition that the normal valence of the atom on which the substitution is considered is not exceeded, and that the substitution results in a compound which is chemically stable, i.e., a compound sufficiently robust to be isolated from a reaction mixture.

The term "alkyl" refers to linear or branched hydrocarbon chains containing the specified number of carbon atoms. For example, C$_1$-C$_6$ alkyl signifies a linear or branched alkyl group containing at least 1 and at most 6 carbon atoms. The term "aryl" refers to an aromatic hydrocarbon ring system containing the specified number of carbon atoms, which is unsubstituted or substituted by an unsubstituted C$_1$-C$_{10}$ alkyl, halogen, NO$_2$, CN, SO$_3$H, or a carbonyl, carboxyl, OH or C$_1$-C$_{10}$ alkoxy moiety. For example, aryl may be a phenyl, naphthyl, anthracyl or phenanthryl. The term "cycloalkyl" refers to a nonaromatic, monocyclic or fused polycyclic hydrocarbon ring system containing the specified number of carbon atoms. For example, cycloalkyl comprises cyclopropyl, cyclobutyl, cyclopentyl, cyclohexyl, cycloheptyl or cyclooctyl. The term "heteroaryl" refers to an aromatic, monocyclic or fused polycyclic hydrocarbon ring system containing the specified number of members, in which at least one of the carbon atoms is replaced by a phosphorus, sulfur, nitrogen or oxygen atom. For example, heteroaryl includes, without limitation, furan, thiophene, pyrrole, imidazole, pyrazole, triazole, tetrazole, thiazole, oxazole, pyridine, pyridazine, pyrazine, indole and indazole. The term "heterocycle" refers to a nonaromatic, monocyclic or fused polycyclic hydrocarbon ring system containing the specified number of members, in which at least one of the carbon atoms is replaced by a phosphorus, sulfur, nitrogen or oxygen atom. For example, heterocycle includes, without limitation, tetrahydrofuran, dihydropyran, tetrahydropyran, pyran, piperidine, pyrrolidine, and dioxane.

Amino Alcohol Compound

According to a first aspect of the present invention, amino alcohol compounds are provided. Said compounds are of formula R$^5$—[C(R$^1$)(R$^2$)]$_u$—R$^6$ (Ia) in which u is an integer between 1 and 10;

R$^1$, R$^2$, R$^5$, and R$^6$ independently for each of the units [C(R$^1$)(R$^2$)]$_u$ and independently of one another represent H, —OR$^{15}$, —OC(O)R$^{15}$, C$_1$-C$_{30}$ alkyl unsubstituted or substituted by one or more groups OR$^{15}$, C$_6$-C$_{12}$ aryl unsubstituted or substituted by one or more groups —OR$^{15}$, C$_3$-C$_{10}$ cycloalkyl unsubstituted or substituted by one or more groups —OR$^{15}$, a group of formula (II), or R$^6$ or R$^5$ and R$^1$ of any one of the units [C(R$^1$)(R$^2$)]$_u$, or R$^1$ of any one of the units [C(R$^1$)(R$^2$)]$_u$ and R$^2$ of any one of the units [C(R$^1$)(R$^2$)]$_u$, form, together with the carbon atoms to which they are attached, a 5- or 6-membered heterocycle, where the croup of formula (II)

(II)

comprises at least 4 carbon atoms and at most 80 carbon atoms, and in which n is an integer between 1 and 15, advantageously between 1 and 10, preferably between 1 and 5;

A independently for each of the units [A]$_n$ is a group of formula —[(X)$_a$—Y—(X)$_b$]— in which Y is C(R)=C(R'), C(R)(CH$_2$NR$^3$R$^4$)—CH(R'), C(R)(CH$_2$OH)—CH(R') or C(R)(R');

X independently for each of the units (X)$_a$ and (X)$_b$ and independently for each of the units [A]$_n$ represents a C$_1$-C$_{10}$ alkyl, C$_6$-C$_{18}$ aryl, C$_3$-C$_{10}$ cycloalkyl, five- to seven-membered heterocycle, five- to seven-membered heteroaryl, or a group of formula —[(C(R")(R'"))$_c$—(Z)—(C(R")(R'"))]$_d$— in which Z is C$_6$-C$_{18}$ aryl, C$_3$-C$_{10}$ cycloalkyl, five- to seven-membered heterocycle or five- to seven-membered heteroaryl;

R, R', R" and R'" independently of one another, independently for each of the units (C(R")(R'")), and independently for each of the units Y represent H, C$_1$-C$_{10}$ alkyl, C$_6$-C$_{12}$ aryl or C$_3$-C$_{10}$ cycloalkyl;

R$^3$ and R$^4$ independently of one another represent H, C$_1$-C$_{10}$ alkyl, C$_6$-C$_{12}$ aryl, benzyl, C$_3$-C$_{10}$ cycloalkyl, or R$^3$ and R$^4$ together with the nitrogen atom to which they are attached form a five- or six-membered heterocycle;

where a, b, c, and d are integers between 0 and 20, advantageously between 0 and 15, preferably between 0 and 10, the sum of a+b or c+d being less than 20;

R$^{15}$ represents H, C$_1$-C$_{30}$ alkyl unsubstituted or substituted by one or more OH groups or by one or more groups of formula (II) as defined above, or five- or six-membered heterocycle unsubstituted or substituted by one or more —OH groups or by one or more groups of formula (II) as defined above;

the compound of formula (Ia) comprising at least one group of formula (II) in which Y is CR(CH$_2$NR$^3$R$^4$)—CHR' in at least one of the units [A]$_n$, and at least one group of formula (II) in which Y is CR(CH$_2$OH)—CHR in at least one of the units [A]$_n$. Accordingly, a single group of formula (II) may comprise one unit [A] in which Y is CR(CH$_2$NR$^3$R$^4$)—CHR' and another unit [A] in which Y is CR(CH$_2$OH)—CHR. Alternatively, the compound may comprise one group Y being CR(CH$_2$NR$^3$R$^4$)—CHR' in one unit [A] of a first group of formula (II), and one group Y being CR(CH$_2$OH)—CHR in one unit [A] of a second group of formula (II).

The group of formula (II) advantageously comprises at least 4 carbon atoms, preferably at least 8 carbon atoms, more particularly at least 10 carbon atoms, more particularly still at least 12 carbon atoms, and not more than 80 carbon atoms, preferably not more than 60 carbon atoms, more particularly not more than 50 carbon atoms, more particularly still not more than 40 carbon atoms.

According to one particular embodiment, the compound according to the present invention may be of formula (Ia) in which at least two of the substituents R$^1$, R$^2$, R$^5$ or R$^6$ independently of one another represent a group of formula (II)

(II)

comprising at least 4 carbon atoms and not more than 80 carbon atoms, and in which n is an integer between 1 and 15, advantageously between 1 and 10, preferably between 1 and 5;

A is selected independently for each of the units [A]$_n$ from the groups of formula (IIa), (IIb), (IIc) or (IId)

—[(CH$_2$)$_q$—CH=CH—(CH$_2$)$_t$]— (IIa),

[(CH$_2$)$_v$—CH(CH$_2$NR$^3$R$^4$)—CH$_2$—(CH$_2$)$_w$]— (IIb),

[(CH$_2$)$_y$—CH(CH$_2$OH)—CH$_2$—(CH$_2$)$_z$]— (IIc),

—[(CH$_2$)$_x$]— (IId), where q, t, v, w, y, and z are integers between 0 and 20, advantageously between 0 and 15, preferably between 0 and 10, the sum of q+t, v+w or y+z being less than 20;

x is an integer between 10 and 30;

the compound of formula (Ia) comprising at least one group of formula (II) in which at least one of the units [A]$_n$ is of formula (IIb), and at least one group of formula (II) in which at least one of the units [A]$_n$ is of formula (IIc).

According to one preferred embodiment, the compound according to the present invention may be of formula (IIIa):

(IIIa)

in which u is an integer between 1 and 7, advantageously between 1 and 6, preferably between 1 and 5, more particularly between 1 and 4, R$^1$, R$^7$, R$^8$, R$^9$, R$^{10}$, R$^5$, and R$^6$ independently of one another and, for R$^1$, independently for each of the units [CHR$^1$]$_u$ represent a moiety of formula (II), H, —OR$^{15}$, C$_1$-C$_{10}$ alkyl unsubstituted or substituted by one or more groups —OR$^{15}$, C$_6$-C$_{12}$ aryl unsubstituted or substituted by one or more groups —OR$^{15}$, C$_3$-C$_{10}$ cycloalkyl unsubstituted or substituted by one or more groups —OR$^{16}$, R$^{15}$ represents H or C$_1$-C$_{10}$ alkyl unsubstituted or substituted by one or more —OH groups, by one or more groups of formula (II) or by a group of formula (IV)

(IV)

in which

R$^{20}$, R$^{21}$, R$^{22}$, and R$^{23}$ independently of one another represent H, —OH, C$_1$-C$_{10}$ alkyl unsubstituted or substituted by one or more groups —OR$^{24}$; R$^{24}$ represents H, C$_1$-C$_{10}$ alkyl unsubstituted or substituted by one or more —OH groups, or one or more groups of formula (II);

the group of formula (II) being represented above, in which n is an integer between 1 and 15, advantageously between 1 and 10, preferably between 1 and 5; A is selected independently for each of the units [A] from the groups of formula (IIa), (IIb), (IIc) or (IId)

[(CH$_2$)$_q$—CH=CH—(CH$_2$)$_t$]— (IIa),

[(CH$_2$)$_v$—CH(CH$_2$NR$^3$R$^4$)—CH$_2$—(CH$_2$)$_w$]— (IIb),

[(CH$_2$)$_y$—CH(CH$_2$OH)—CH$_2$—(CH$_2$)$_z$]— (IIc),

—[(CH$_2$)$_x$]— (IId),

R$^3$ and R$^4$ independently of one another represent H, C$_1$-C$_{10}$ alkyl, C$_6$-C$_{12}$ aryl, benzyl or C$_3$-C$_{10}$ cycloalkyl, or R$^3$ and R$^4$ with the nitrogen atom to which they are attached form a five- or six-membered heterocycle; where q, t, v, w, y, and z are integers between 0 and 20, advantageously between 0 and 15, preferably between 0 and 10, the sum of q+t, v+w or y+z being less than 20; x is an integer between 10 and 30; the compound of formula (IIIa) comprising at least one group of formula (II) in which at least one of the units [A]$_n$ is of formula (IIb), and at least one group of formula (II) in which at least one of the units [A]$_n$ is of formula (IIc) as defined above.

Preferably, in this preferred embodiment, at least two of the substituents R$^1$, R$^5$, and R$^6$ independently of one another represent a group of formula (II) in which n is 1 and A is a group of formula (IIb) or (IIc).

According to another preferred embodiment, the compound according to the present invention may be of formula (IIIb):

in which
R$^1$, R$^2$, R$^5$, and R$^6$ independently of one another represent a group of formula (II), —OR$^{15}$, C$_1$-C$_{10}$ alkyl unsubstituted or substituted by one or more groups —OR$^{15}$, R$^{15}$ represents H, C$_1$-C$_{10}$ alkyl unsubstituted or substituted by one or more —OH groups, or one or more groups of formula (II) or a group of formula (IV);
the group of formula (II) being represented above, in which n is an integer between 1 and 15, advantageously between 1 and 10, preferably between 1 and 5; A is selected independently for each of the units [A] from the groups of formula (IIa), (IIb), (IIc) or (IId)

[(CH$_2$)$_q$—CH=CH—(CH$_2$)$_t$]—      (IIa),

[(CH$_2$)$_v$—CH(CH$_2$NR$^3$R$^4$)—CH$_2$—(CH$_2$)$_w$]—      (IIb),

[(CH$_2$)$_y$—CH(CH$_2$OH)—CH$_2$—(CH$_2$)$_z$]—      (IIc), —[(CH$_2$)$_x$]—      (IId), R$^3$ and R$^4$ independently of one another represent H, C$_1$-C$_{10}$ alkyl, C$_6$-C$_{12}$ aryl, benzyl, C$_3$-C$_{10}$ cycloalkyl, or R$^3$ and R$^4$ with the nitrogen atom to which they are attached form a five- or six-membered heterocycle; where q, t, v, w, y, and z are integers between 0 and 20, advantageously between 0 and 15, preferably between 0 and 10, the sum of q+t, v+w or y+z being less than 20; x is an integer between 10 and 30; the compound of formula (IIIb) comprising at least one group of formula (II) in which at least one of the units [A]$_n$ is of formula (IIb), and at least one group of formula (II) in which at least one of the units [A]$_n$ is of formula (IIc) as defined above.

Preferably, in this embodiment, R$^5$ represents a group of formula (II) in which n is 1 and A is of formula (IIb), and R$^6$ represents a group of formula (II) in which n is 1 and A is of formula (IIa).

According to another preferred embodiment, the compound according to the present invention may be of formula (IIIc):

in which
R$^5$ represents a group of formula (II) in which
n is an integer between 1 and 15, advantageously between 1 and 10, preferably between 1 and 5; A is a group of formula

[(CH$_2$)$_v$—CH(CH$_2$NR$^3$R$^4$)—CH$_2$—(CH$_2$)$_w$]—      (IIb), R$^3$ and R$^4$ independently of one another represent H, C$_1$-C$_{10}$ alkyl, C$_6$-C$_{12}$ aryl, benzyl, C$_3$-C$_{10}$ cycloalkyl, or R$^3$ and R$^4$ with the nitrogen atom to which they are attached form a five- or six-membered heterocycle; where v and w are integers between 0 and 20, advantageously between 0 and 15, preferably between 0 and 10, the sum of v+w being less than 20; and
R$^6$ represents a group of formula (II) in which
n is an integer between 1 and 15, advantageously between 1 and 10, preferably between 1 and 5; A is a group of formula

[(CH$_2$)$_y$—CH(CH$_2$OH)—CH$_2$—(CH$_2$)$_z$]—      (IIc), where y and z are integers between 0 and 20, advantageously between 0 and 15, preferably between 0 and 10, the sum of v+w being less than 20.

According to one particular embodiment, the compound according to the present invention is of formula (IIIa) in which
u is an integer between 1 and 5, preferably between 1 and 4;
R$^7$, R$^8$, R$^9$ and R$^{10}$ represent a hydrogen,
R$^1$, R$^5$, and R$^6$ independently of one another and, for R$^1$, independently for each of the units [CHR$^1$]$_u$ represent a group of formula (II) in which A is selected independently for each of the units [A]$_n$- from the groups of formula (IIa), (IIb) or (IIc);
the compound of formula (IIIa) comprising at least one group of formula (II) in which at least one of the units [A]$_n$ is of formula (IIb), and at least one group of formula (II) in which at least one of the units [A]$_n$ is of formula (IIc).

The compound according to the present invention may be of formula (IIIa) in which
u is an integer between 1 and 5, preferably between 1 and 4;
R$^7$, R$^8$, R$^9$, and R$^{10}$ represent a hydrogen,
R$^1$, R$^5$, and R$^6$ independently of one another and, for R$^1$, independently for each of the units [CHR$^1$]$_u$ represent a group of formula (II) in which n is 1 and A is selected independently for each of the units [A]$_n$- from the groups of formula (IIa), (IIb) or (IIc); the compound (IIIa) comprising at least one group of formula (II) in which A is (IIb) and at least one group of formula (II) in which A is (IIc).

The compound according to the present invention may be of formula (IIIa) in which
R$^7$, R$^8$, R$^9$, and R$^{10}$ represent a hydrogen,
u is 1,
R$^1$, R$^5$, and R$^6$ independently of one another represent a group of formula (II) in which A is selected independently for each of the units [A]$_n$- from the groups of formula (IIb) or (IIc),
where R$^3$, R$^4$, v, w, y, and z are as defined above;
n is an integer between 1 and 5;
each of the substituents R$^1$, R$^5$, and R$^6$ comprising at least 12 carbon atoms and at most 25 carbon atoms,
the compound of formula (IIIa) comprising at least one group of formula (II) in which at least one of the units [A]$_n$ is of formula (IIb), and at least one group of formula (II) in which at least one of the units [A]$_n$ is of formula (IIc).

The compound of formula (IIIa) may comprise more groups of formula (II) in which at least one of the units [A]$_n$ is of formula (IIb) than groups of formula (II) in which at least one of the units [A]$_n$ is of formula (IIc). Alternatively, the compound of formula (IIIa) may comprise fewer groups of formula (II) in which at least one of the units [A]$_n$ is of formula (IIb) than groups of formula (II) in which at least one of the units $[A]_n$ is of formula (IIc).

More particularly, the compound according to the present invention may be of formula (IIIa) in which $R^7$, $R^8$, $R^9$, and $R^{10}$ represent a hydrogen and u is 1, $R^1$, $R^5$ and $R^6$ independently of one another represent a group of formula (II) in which n is 1, A is a group of formula (IIb) or (IIc)

$[(CH_2)_v—CH(CH_2NR^3R^4)—CH_2—(CH_2)_w]—$  (IIb), or $[(CH_2)_y—CH(CH_2OH)—CH_2—(CH_2)_z]—$  (IIc);

$R^3$ and $R^4$ independently of one another represent H, $C_1$-$C_{10}$ alkyl, $C_6$-$C_{12}$ aryl, benzyl, $C_3$-$C_{10}$ cycloalkyl, or $R^3$ and $R^4$ together with the nitrogen atom to which they are attached form a five- or six-membered heterocycle;

v, y, w, and z independently of one another are an integer between 4 and 9, where v+w or y+z is an integer between 11 and 15, the compound of formula (IIIa) comprising at least one group of formula (II) in which A is of formula (IIb) and at least one group of formula (II) in which A is of formula (IIc); preferably, the compound of formula (IIIa) comprises one group of formula (II) in which A is of formula (IIb) and two groups of formula (II) in which A is of formula (IIc), or two groups of formula (II) in which A is of formula (IIb) and one group of formula (II) in which A is of formula (IIc).

Preparation Process

According to a second aspect of the present invention, a process for preparing amino alcohol is provided. The process permits, in a single step, the hydroaminomethylation of a first carbon-carbon double bond and the hydrohydroxymethylation of a second carbon-carbon double bond, i.e. the hydrogenation of aldehydes formed in situ by hydroformylation of said second carbon-carbon double bond. Thus, the hydrogenation of aldehydes formed in situ allows alcohol to be formed. More particularly, the present invention provides a process for preparing amino alcohol from a compound B comprising at least two carbon-carbon double bonds, said process comprising a step a) of combining with stirring, in a reactor, at least one precatalyst, an amine of formula $HNR^3R^4$ in which $R^3$ and $R^4$ independently of one another represent H, $C_1$-$C_{10}$ alkyl, $C_6$-$C_{12}$ aryl, $C_3$-$C_{10}$ cycloalkyl, or $R^3$ and $R^4$ together with the nitrogen atom to which they are attached form a five- or six-membered heterocycle; and said compound B, in an atmosphere of hydrogen and carbon monoxide. Said process allows the preparation of a compound in which one carbon atom of at least one of the carbon-carbon double bonds in the compound B has been substituted by a moiety $CH_2NR^3R^4$, the other carbon atom of this same carbon-carbon double bond being substituted by a hydrogen; and in which one carbon atom of at least one other of the carbon-carbon double bonds in the compound B has been substituted by a $CH_2OH$ moiety, the other carbon atom of this same carbon double bond being substituted by a hydrogen. The carbon-carbon double bonds present in the compound B may be of cis or trans configuration. The term "carbon-carbon double bond" encompasses both configurations.

Figure 1:
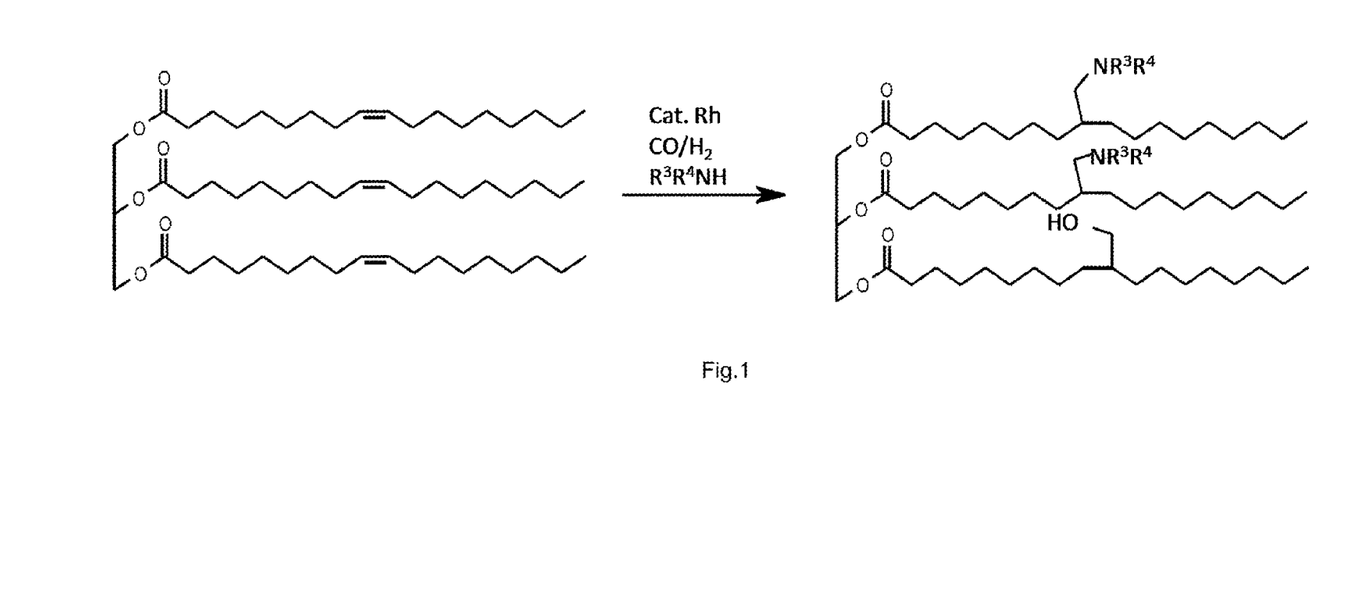
FIG. 1 represents a scheme of the synthesis of amino alcohol compounds according to one particular embodiment of the invention.

FIG. 1 illustrates the process according to one particular embodiment of the present invention, involving a hydroaminomethylation and hydrohydroxymethylation reaction. The compound B is represented by triolein, which comprises three carbon-carbon double bonds. The process according to the present invention thus allows the preparation of an amino alcohol compound in which two of the three carbon-carbon double bonds are hydroaminomethylated while the third carbon-carbon double bond is hydrohydroxymethylated.

The present process is therefore carried out under the pressure of an atmosphere of hydrogen and carbon monoxide. The pressure may be between 10 bar and 200 bar, advantageously between 20 bar and 150 bar, preferably between 50 bar and 100 bar. The pressure relates to the sum of the partial pressures of carbon monoxide and of hydrogen. The molar ratio of carbon monoxide to hydrogen is between 1:10 and 10:1; advantageously, the molar ratio of carbon monoxide to hydrogen is between 1:5 and 5:1; preferably, the molar ratio is between 1:3 and 3:1; more particularly, the molar ratio of carbon monoxide to hydrogen is between 1:2 and 2:1. More particularly, the molar ratio of carbon monoxide to hydrogen is 1:2.

Said compound B may advantageously be of formula (V')
$R^a—[C(R^d)(R^e)]_u—R^f$ in which
u is an integer between 1 and 10
$R^a$, $R^d$, $R^e$, and $R^f$, independently of one another and independently for each of the units $[C(R^d)(R^e)]_u$, represent H, $—OR^j$, $—O—C(O)—R^j$, $C_1$-$C_{30}$ alkyl unsubstituted or substituted by one or more groups $—OR^j$, $C_6$-$C_{12}$ aryl unsubstituted or substituted by one or more groups $—OR^j$, $C_3$-$C_{10}$ cycloalkyl unsubstituted or substituted by one or more groups $—OR^j$, a group of formula (V), or $R^a$ or $R^f$ and $R^d$ of any one of the units $[C(R^d)(R^e)]_u$, or $R^d$ of any one of the units $[C(R^d)(R^e)]_u$ and $R^e$ of any one of the units $[C(R^d)(R^e)]_u$, together with the carbon atoms to which they are attached, form a 5- or 6-membered heterocycle, the group of formula (V) comprising at least 3 carbon atoms and not more than 79 carbon atoms, and being of formula $—O—C(O)_n—H$ (V) in which A is $—(X)_a—C(R)=C(R')—(X)_b—$ n is an integer between 1 and 10, preferably between 1 and 6;

X, independently for each of the units $(X)_a$ and $(X)_b$ and independently for each of the units [A], represents a $C_1$-$C_{10}$ alkyl, $C_6$-$C_{18}$ aryl, $C_3$-$C_{10}$ cycloalkyl, five- to seven-membered heterocycle, five- to seven-membered heteroaryl, or a group of formula $[(C(R'')(R'''))_c—(Z)—(C(R'')(R'''))_d]$ in which Z is $C_6$-$C_{18}$ aryl, $C_3$-$C_{10}$ cycloalkyl, five- to seven-membered heterocycle or five- to seven-membered heteroaryl;

where a, b, c, and d are integers between 0 and 20, advantageously between 0 and 15, preferably between 0 and 10, the sum of a+b being less than 20;

R, R', R'', and R''' independently of one another, independently for each of the units (C(R')(R'')), and independently for each of the units Y represent H, $C_1$-$C_{10}$ alkyl, $C_6$-$C_{12}$ aryl or $C_3$-$C_{10}$ cycloalkyl;

$R^j$ represents H, $C_1$-$C_{30}$ alkyl unsubstituted or substituted by one or more OH groups, $C_1$-$C_{30}$ alkyl unsubstituted or substituted by one or more groups of formula (V) as defined above, a five- or six-membered heterocycle unsubstituted or substituted by one or more OH groups, or a five- or six-membered heterocycle unsubstituted or substituted by one or more groups of formula (V) as defined above;

the compound B of formula (V') comprising at least two groups of formula (V) or one group of formula (V) in which n is at least 2, for preparing a compound according to the present invention of formula (Ia).

The group of formula (V) is preferably of formula (Va), comprising at least 3 carbon atoms and not more than 79 carbon atoms, $—O—C(O)—[—(CH_2)_p—C=C—(CH_2)_s—]_r—H$  (Va)

in which
- r is an integer between 1 and 15, advantageously between 1 and 10, preferably between 1 and 6, more particularly between 1 and 5;
- where p and s are integers between 0 and 20, advantageously between 0 and 15, preferably between 0 and 10, the sum of p+s being less than 20 and greater than 1;
- the compound B of formula (V') comprising at least two groups of formula (Va) or one group of formula (Va) in which r is at least 2.

The carbon-carbon double bonds present in the group of formula (Va) may be of cis or trans configuration.

Said compound B is more particularly of formula (VIa), (VIb) or (VIc):

(VIa)

in which
- u is an integer between 1 and 7, advantageously between 1 and 6, preferably between 1 and 5, more particularly between 1 and 4,
- $R^d$, $R^b$, $R^c$, $R^g$, $R^h$, $R^a$, and $R^f$ independently of one another and, for $R^d$, independently for each of the units $[CHR^d]_u$, represent a moiety of formula (Va) as defined above, H, $-OR^j$, $C_1$-$C_{10}$ alkyl unsubstituted or substituted by one or more groups $-OR^j$, $C_6$-$C_{12}$ aryl unsubstituted or substituted by one or more groups $-OR^j$, $C_3$-$C_{10}$ cycloalkyl unsubstituted or substituted by one or more groups $-OR^j$,
- $R^j$ represents H, $C_1$-$C_{10}$ alkyl unsubstituted or substituted by one or more $-OH$ groups, by one or more groups of formula (Va) as defined above, or by a group of formula (IV)

(IV)

in which
- $R^{20}$, $R^{21}$, $R^{22}$, and $R^{23}$ independently of one another represent H, $-OH$, $C_1$-$C_{10}$ alkyl unsubstituted or substituted by one or more groups $OR^{24}$; $R^{24}$ represents H, $C_1$-$C_{10}$ alkyl unsubstituted or substituted by one or more $-OH$ groups, or by one or more groups of formula (Va) as defined above;

or (VIb)

in which
- $R^e$, $R^f$, $R^d$, and $R^e$ independently of one another represent a group of formula (Va) as defined above, $-OR^j$, or $C_1$-$C_{10}$ alkyl unsubstituted or substituted by one or more groups $-OR^j$,
- $R^j$ represents H, $C_1$-$C_{10}$ alkyl unsubstituted or substituted by one or more $-OH$ groups, by one or more groups of formula (Va) as defined above, or by a group of formula (IV);

or (VIc)

in which
- $R^e$ and $R^f$ independently of one another represent a group of formula (Va) as defined above;

the compound of formula (VIa), (VIb) or (VIc) comprising at least two groups of formula (Va) as defined above or a group of formula (Va) as defined above in which r is at least 2. Accordingly, compounds of formula (IIIa), (IIIb) or (IIIc) according to the present invention may be prepared.

More particularly, said compound B is of formula (VIa)

(VIa)

in which
- $R^b$, $R^c$, $R^g$, and $R^h$ represent a hydrogen,
- u is an integer between 1 and 5, advantageously between 1 and 4, u preferably being 1;
- $R^a$, $R^d$, and $R^f$ independently of one another and, for $R^d$, independently for each of the units $[CHR^d]_u$, represent a group of formula (Va) as defined above.

Preferably, said compound B is of formula (VIa) in which $R^b$, $R^c$, $R^g$, and $R^h$ represent a hydrogen, u is 1, $R^d$, $R^a$ and $R^f$ independently of one another represent a group of formula (Va) as defined above in which r is 1, p and s independently of one another are between 4 and 9, with p+s being between 10 and 14.

According to one preferred embodiment, step a) of the present process is carried out at a temperature between 25° C. and 150° C., advantageously between 35° C. and 120° C., preferably between 50° C. and 120° C.

Preferably, step a) is carried out at a temperature between 25° C. and 65° C., advantageously between 25° C. and 55° C. Within this temperature range, the hydroformylation of the carbon-carbon double bond and then the reduction to alcohol of the carbonyl group (hydrohydroxymethylation reaction) is promoted. Accordingly, the preparation of a compound of formula (IIIa) in which the number of unit A of formula (IIc) is greater than the number of unit A of formula (IIb) may be promoted.

Alternatively, step a) is carried out at a temperature between 65° C. and 150° C., advantageously between 70° C. and 120° C. Within this temperature range, the hydroaminomethylation of the carbon-carbon double bond is promoted. Accordingly, the preparation of a compound of formula (IIIa) in which the number of unit A of formula (IIb) is greater than the number of unit A of formula (IIc) may be promoted.

According to one preferred embodiment, the proportion of amine employed in step a) of the present process is greater than 0.8 equivalent in relation to the quantity of compound B employed in step a), the proportion advantageously being between 0.8 and 2 equivalents, preferably between 0.8 and 1.5 equivalents. In this embodiment, the preparation, from a compound B of formula (V'), of a compound of formula (Ia) comprising less of unit A in which Y is $CR(CH_2NR^3R^4)$—CHR' than of unit A in which Y is $CR(CH_2OH)$—CHR is promoted. More particularly, the preparation, from a compound B of formula (VIa) with u=1, of a compound of formula (IIIa) in which u is 1 and comprising one unit A of formula (IIb) and two units A of formula (IIc) is promoted.

According to an alternative embodiment, the proportion of amine employed in step a) of the present process is less than 0.8 equivalent in relation to the quantity of compound B employed in step a), the proportion advantageously being between 0.1 and 0.8 equivalents, preferably between 0.2 and 0.7 equivalents. In this embodiment, the preparation of a compound of formula (Ia) according to the present invention comprising more of unit A in which Y is $CR(CH_2NR^3R^4)$—CHR' than of unit A in which Y is $CR(CH_2OH)$—CHR is promoted. More particularly, the preparation, from a compound B of formula (VIa) with u=1, of a compound of formula (IIIa) in which u is 1 and comprising two units A of formula (IIb) and one unit A of formula (IIc) is promoted.

According to one preferred embodiment, the precatalyst is a complex comprising a transition metal selected from columns 8 to 10 of the periodic table, the transition metal being selected advantageously from column 9 of the periodic table; preferably, the precatalyst is a complex comprising a transition metal selected from rhodium or cobalt. The precatalyst may comprise one or more ligands. At least one of said one or more ligands is selected from CO, acetylacetonate, cyclooctadiene, norbornene, acetate.

Said one or more ligands may also comprise at least one monodentate or bidentate phosphorus ligand comprising at least one $C_6$-$C_{18}$ aryl substituent substituted in ortho position relative to the phosphorus atom or comprising at least one $C_6$-$C_{18}$ aryloxy substituent. Said phosphorus ligand may advantageously be of formula $P(Ar)_3$ or $(Ar)_2$—P-L-P$(Ar)_2$ in which Ar is a $C_6$-$C_{18}$ aryl moiety substituted at least in ortho position relative to the phosphorus atom by a moiety selected from the group consisting of $C_1$-$C_6$ alkyl, phenyl, benzyl, $C_3$-$C_6$ cycloalkyl, halogen, $C_1$-$C_6$ alkoxy, $C_6$ aryloxy; and L is a spacer arm selected from the group consisting of $C_1$-$C_6$ alkyl, $C_6$-$C_{12}$ aryl, $C_3$-$C_{10}$ cycloalkyl. The expression "substituted in ortho position relative to the phosphorus atom" signifies that, in the aryl ring system, at least one of the two ortho positions relative to the carbon atom bonded to the phosphorus atom is substituted by one of said moieties. Said phosphorus ligand may preferably be of formula $P(Ar)_3$ in which Ar is a $C_6$-$C_{18}$ aryl moiety substituted in ortho position relative to the phosphorus atom by a moiety selected from the group consisting of methyl, ethyl, methoxy, phenyl, benzyl, —F, and cyclohexyl.

Alternatively, said phosphorus ligand may be of formula $P(O$—$Ar)_3$ or $(Ar$—$O)_2$—P-L-P$(O$—$Ar)_2$ in which Ar is a $C_6$-$C_{18}$ aryl moiety unsubstituted or substituted by a moiety selected from the group consisting of $C_1$-$C_6$ alkyl, $C_3$-$C_6$ alkyl, halogen, $C_1$-$C_6$ alkoxy, $C_6$ aryloxy; and L is a spacer arm selected from the group consisting of $C_1$-$C_6$ alkyl, $C_6$-$C_{12}$ aryl, and $C_3$-$C_{10}$ cycloalkyl. Said phosphorus ligand may preferably be of formula $P(O$—$Ar)_3$ in which Ar is a $C_6$ aryl unsubstituted or substituted by a methyl, ethyl, methoxy, phenyl, benzyl or cyclohexyl moiety.

Said phosphorus ligand may more particularly be $P(OPh)_3$, $P(C_6F_5)_3$, $P(o$-$MePh)_3$, $P(o$-$OMePh)_3$.

Alternatively, said one or more ligands also comprise at least one water-soluble, monodentate or bidentate phosphorus ligand comprising at least one functional moiety $SO_3^-$ $X^+$, $NR_3^+A^-$, $CO_2^-X^+$, where X represents Li, Na or K; and A represents Cl, Br or I. Said phosphorus ligand may advantageously be of formula $P(Ar)_3$ or $(Ar)_2$—P-L-P$(Ar)_2$ in which L is a spacer arm selected from the group consisting of $C_1$-$C_6$ alkyl, $C_6$-$C_{12}$ aryl, $C_3$-$C_{10}$ cycloalkyl; and Ar is a $C_6$-$C_{18}$ aryl substituted by at least one functional moiety $SO_3^-X^+$, $NR_3^+A^-$, $CO_2^-X^+$, where X represents Li, Na or K, and A represents Cl, Br or I; and optionally substituted by a moiety selected from the group consisting of $C_1$-$C_6$ alkyl, phenyl, benzyl, $C_3$-$C_6$ cycloalkyl, halogen, $C_1$-$C_6$ alkoxy and $C_6$ aryloxy.

According to one particular embodiment, step a) also combines an -α, -β, -γ methyl cyclodextrin having an average degree of substitution of between 0.5 and 2.0 or an -α, -β, -γ hydroxyl cyclodextrin having an average degree of substitution of between 0.5 and 0.9. Said -α, -β, -γ methyl cyclodextrin may have an average degree of substitution of between 1.6 and 2.0, or between 0.9 and 1.6 or between 0.5 and 0.9. When a cyclodextrin and a water-soluble phosphorus ligand as stated above are used in step a), water is also added to this same step a) in order to create a two-phase medium comprising an organic phase and an aqueous phase. Before the reaction is carried out, the organic phase consists in particular of the compound B according to the present invention and the amine. In this embodiment, the compound B is of formula (VIa) according to the present invention, and the amine is of formula $HNR^3R^4$ in which $R^3$ and $R^4$ independently of one another represent $C_4$-$C_{10}$ alkyl, $C_6$-$C_{12}$ aryl, $C_3$-$C_{10}$ cycloalkyl, with $R^3$ and $R^4$ preferably representing independently of one another $C_4$-$C_{10}$ alkyl. When the process is carried out in the presence of a cyclodextrin, the precatalyst comprises at least one water-soluble, monodentate or bidentate phosphorus ligand as defined above. Moreover, the process in that case is carried out under operating conditions which permit the establishment of an emulsion during stirring, and decanting of the products of the reaction after the stirring is halted, preferably the decanting of at least part of the compound according to the present invention. The proportion of cyclodextrin is advantageously between 15 and 40% by weight, based on the total weight of water, cyclodextrin, and compound B of formula (V') or (VIa) or (VIb) or (VIc) combined in step a).

Alternatively, according to one particular embodiment, when the precatalyst comprises a water-soluble phosphorus ligand, step a) may also combine a cosolvent of formula $R^pOH$ in which $R^p$ represents a $C_1$-$C_{10}$ alkyl, a $C_6$-$C_{12}$ aryl or a $C_3$-$C_{10}$ cycloalkyl; $R^p$ advantageously represents a $C_1$-$C_4$ alkyl, the cosolvent preferably being isopropanol. The cosolvent may replace the cyclodextrin. A neutral surfactant comprising a hydroxyl-containing polar group may optionally also be added.

The process according to the present invention may also comprise a step of recycling when the process is carried out in a two-phase medium. The recycling step comprises the degassing of the reactor in which the process according to the present invention is carried out, the withdrawal of the organic phase under a controlled atmosphere, and the addition to the reactor of said compound B and the amine and optionally of one or more ligands as described above. During this recycling step, the temperature remains constant, in other words remains at the temperature at which the hydroaminomethylation and hydrohydroxymethylation reactions were carried out.

EXAMPLES

Determination of the Selectivity for Amine or for Alcohol

The reaction products before purification were characterized by nuclear magnetic resonance (NMR) in deuterated chloroform (CDCl$_3$). The NMR analyses are carried out on a BRUKER 300 MHz instrument. The selectivities for aldehydes, amines, alcohols, and hydrogenated C=C of which the products obtained from the reaction are capable are determined by integration of the $^1$H NMR signals. The reaction products were also characterized by mass spectrometry via matrix-assisted laser ionization (MALDI). The mass spectrometry is performed on a sample prepared in a 2,5-dihydroxybenzoic acid matrix (DHB).

The structure of the reaction products was confirmed by subjecting them to transesterification and then analyzing the transesterification products by $^1$H NMR. The transesterification was carried out in the presence of methanol to give the corresponding methyl esters, which can be separated by liquid chromatography on silica, with, for example, a heptane/ethyl acetate gradient.

Example 1

A reactor is charged with 1 mL of triolein (1 mmol), 5 mL of toluene, 3.9 mg of Rh(CO)$_2$(acac) (0.015 mmol), and 530 μL of dibutylamine (3.3 mmol). The reaction is carried out under a pressure of 80 bar of carbon monoxide and hydrogen (molar ratio 1:1) for 18 hours.

Figure 2:
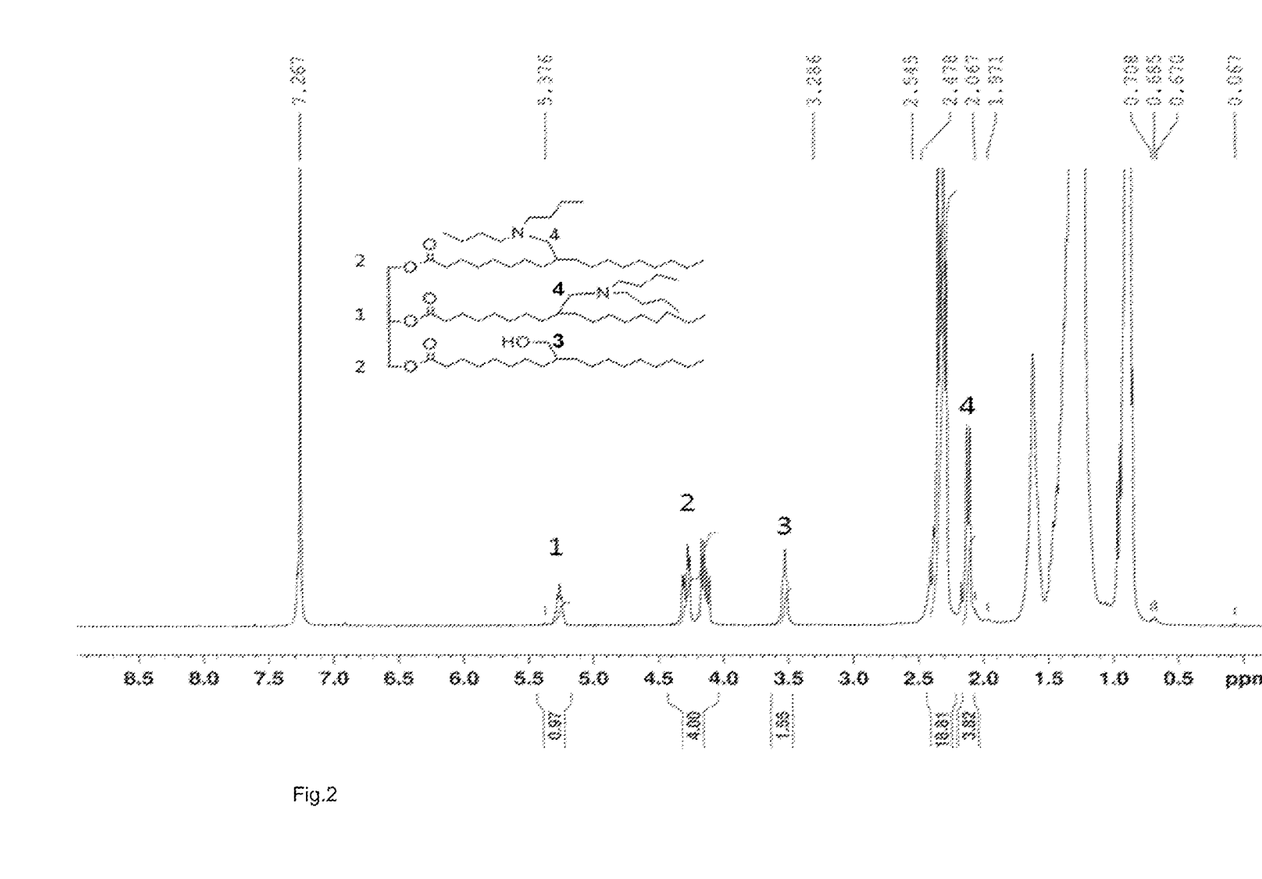
FIG. 2 represents an NMR spectrum of an amino alcohol compound according to the present invention.

Table 1 below reports the results obtained at different temperatures. The products obtained comprise on average two amine functions and one alcohol function when the reaction temperature is 80° C. or 100° C. (examples 1a and 1b). FIG. 2 shows a $^1$H NMR spectrum of the product obtained and the formula thereof. The peak labeled 1 on the NMR spectrum of FIG. 2 corresponds to the hydrogen atom carried by the carbon atom labeled 1 in the glycerol unit. The peak labeled 2 on the NMR spectrum of FIG. 2 corresponds to the hydrogen atoms carried by the carbon atoms labeled 2 in the glycerol unit. The peak labeled 3 on the NMR spectrum of FIG. 2 corresponds to the hydrogen atoms carried by the carbon atom labeled 3. The peak labeled 4 on the NMR spectrum of FIG. 2 corresponds to the hydrogen atoms carried by the carbon atoms labeled 4. The selectivity of the reaction is oriented toward the preferential formation of alcohol function when the temperature is 50° C. (example 1c).

TABLE 1

Catalytic performance as a function of temperature

| Ex. | T (° C.) | Conversion$^a$ (%) | Selec.$^b$ Aldehyde | Selec.$^b$ Alcohol | Selec.$^b$ Amine | Selec.$^b$ Hydrogenation | Ratio alcohol/amine$^c$ |
|---|---|---|---|---|---|---|---|
| 1a | 80 | 100 | 0 | 28 | 68 | 4 | 0.41 |
| 1b | 100 | 100 | 0 | 20 | 79 | 1 | 0.25 |
| 1c | 50 | 76 | 0 | 55 | 44 | 1 | 1.25 |

$^a$(number of moles of C=C converted in the triglyceride, divided by the total number of moles of C=C in the triglyceride) × 100.
$^b$(molar number of a given function divided by the molar number of C=C converted) × 100.
$^c$proportion of alcohol functions in relation to the amine functions in the aminohydroxylated triglyceride.

Example 1 demonstrates that the temperature provides an easy way of prioritizing either a hydroaminomethylation reaction or a hydrohydroxymethylation reaction.

Example 2

Example 1 was reproduced for a temperature of 80° C. with variation in the amine and in its concentration. Table 2 summarizes the results obtained.

TABLE 2

Catalytic performance as a function of the type and concentration of the amine

| Ex. | Amine | Conversion$^a$ (%) | Selec.$^b$ Aldehyde | Selec.$^b$ Alcohol | Selec$^b$ Amine | Selec.$^b$ Hydrogenation | Ratio alcohol/amine$^c$ |
|---|---|---|---|---|---|---|---|
| 2a | HN(Et)$_2$$^d$ | 100 | 0 | 27 | 65 | 8 | 0.41 |
| 2b | H$_2$N(Hex)$^e$ | 100 | 0 | 33 | 60 | 7 | 0.55 |
| 2c | HN(Et)$_2$$^f$ | 100 | 0 | 51 | 46 | 3 | 1.1 |
| 2d | HN(Et)$_2$$^g$ | 100 | 0 | 79 | 19 | 2 | 4.16 |

$^a$(number of moles of C=C convened in the triglyceride, divided by the total number of moles of C=C in the triglyceride) × 100.
$^b$(molar number of a given function divided by the molar number of C=C converted) × 100.
$^c$proportion of alcohol functions in relation to the amine functions in the aminohydroxylated triglyceride.
$^d$diethylamine (3.3 mmol);
$^e$hexylamine (3.3 mmol);
$^f$diethylamine (2 mmol);
$^g$diethylamine (1 mmol).

The results summarized in table 2 show an effect of the concentration of the amine on the selectivity of the end product. Hence, with a paucity of amine in the reaction mixture, the formation of alcohol moiety by a hydrohydroxymethylation reaction is promoted. Under conditions of stoichiometry between the amine and the triolein, the formation of a compound comprising more amine functions than alcohol functions is promoted.

Example 3

In a reactor, 1 mL of triolein (1 mmol), 5 mL of toluene, 3.9 mg of Rh(CO)$_2$(acac) (0.015 mmol), and 530 μL of dibutylamine (3.3 mmol) are mixed. A phosphine is also added to the reaction mixture in proportions of the order of one equivalent or 5 equivalents in relation to the precatalyst. The reaction is carried out under a pressure of 80 bar of carbon monoxide and hydrogen (molar ratio 1:1) for 18 hours at a temperature of 80° C. Example 3d employs a water-soluble phosphine, and in that case the toluene is replaced by a mixture composed of 5 mL of water and 2 mL of isopropanol. Example 3e employs a water-soluble phosphine and a modified cyclodextrin. Table 3 below shows the results obtained.

TABLE 3

Catalytic performance as a function of the type and concentration of the phosphine

| Ex. | Phosphine | Conversion[a] (%) | Selec.[b] Aldehyde | Selec.[b] Alcohol | Selec.[b] Amine | Selec.[b] Hydrogenation | Ratio alcohol/amine[c] |
|---|---|---|---|---|---|---|---|
| 3a | o(Me)$_3$TPP | 100 | 0 | 27 | 74 | 1 | 0.36 |
| 3b | o(Me)$_3$TPP | 100 | 0 | 31 | 68 | 1 | 0.46 |
| 3c | o(OMe)$_3$TPP | 100 | 0 | 22 | 77 | 1 | 0.29 |
| 3d | o(Me)$_3$TPPTS | 63 | 9 | 57 | 29 | 5 | 1.96 |
| 3e | TPPTS + CRYSMEB ® | 88 | 1 | 76 | 21 | 2 | 3.62 |

[a](number of moles of C=C converted in the triglyceride, divided by the total number of moles of C=C in the triglyceride) × 100.
[b](molar number of a given function divided by the molar number of C=C converted) × 100.
[c]proportion of alcohol functions in relation to the amine functions in the aminohydroxylated triglyceride.
3a - o(Me)$_3$TPP: Tri(ortho-tolyl)phosphine 0.015 mmol;
3b - o(Me)$_3$TPP: Tri(ortho-tolyl)phosphine 0.075 mmol;
3c - o(OMe)$_3$TPP: Tri(ortho-methoxyphenyl)phosphine 0.015 mmol;
3d - P(2-(Me)-4-(SO$_3$Na)—Ph)$_3$ 0.075 mmol;
3e - P(3-SO3Na—Ph)3 (trisodium salt of triphenylphosphine trisulfonated in meta position) 0.075 mmol + 2.3 g of Crysmeb ® (cyclodextrin partially methylated on the 2 hydroxyls with an average degree of substitution per glucopyranose unit of 0.8)

Very good results are obtained when a phosphine is added as ligand of the precatalyst. The hydroaminomethylation reaction is promoted in a homogeneous medium and in the presence of an ortho-hindered phosphine (examples 3a-3c).

The conversion and the selectivity of the reaction are maintained even in the presence of an excess of phosphine relative to the precatalyst (example 3b). Example 3d, which employs a water-soluble phosphine in a two-phase medium, tends to promote the formation of a product comprising more alcohol functions than amine functions. This is promoted all the more when a methyl cyclodextrin having a degree of substitution of 0.8 is added (example 3e).

Example 4

A reactor is charged with 1 mL of triolein (1 mmol), 5 mL of toluene, 3.9 mg of Rh(CO)$_2$(acac) (0.015 mmol), and 530 μL of dibutylamine (3.3 mmol). The reaction is carried out under a pressure of 80 bar of carbon monoxide and hydrogen for 6 hours.

The experiments below provide examples of the use of different molar ratios of the CO/H$_2$ synthesis gas used in this reaction. This ratio is varied by introducing partial pressures of the different gases, CO and H$_2$, successively into the autoclave. The gas mixture therefore possesses a stoichiometry which is equal to the ratio of the different partial pressures.

TABLE 4

Effect of the CO/H$_2$ ratio on the amino alcohol synthesis reaction.[a]

| Ex.° | Partial pressure CO (bar) | Partial pressure H$_2$ (bar) | Ratio CO/H$_2$ | Conv. (%) | Selec. Aldehyde (%) | Selec. Alcohol (%) | Selec. Amine (%) | Selec. Hydrogenation (%) |
|---|---|---|---|---|---|---|---|---|
| 4a | 40 | 40 | 1 | 95 | 0 | 25 | 72 | 3 |
| 4b | 26 | 54 | 0.5 | 94 | 0 | 44 | 55 | 1 |

[a]Conditions: 1 mL of triolein (1 mmol, 3 mmol of double bonds); toluene: 5 mL; Rh(CO)$_2$(acac): 3.9 mg, (0.015 mmol); amine: NH(Bu)$_2$: 530 μL (3.3 mmol), 80° C., total pressure: 80 bar, 6 h.

These results show that the CO/H$_2$ molar ratio may guide the reaction toward the preferential formation of alcohol functions or of amine functions. The reason is that increasing the partial pressure of H$_2$ in the medium increases the proportion of alcohol at the expense of the formation of tertiary amine.

The process according to the present invention therefore allows the selective preparation of fatty amino alcohol compounds as described in the present specification.

The terms and descriptions used here are given by way of illustration only and do not constitute limitations. The skilled person will recognize that many variations are possible within the spirit and the scope of the invention as described in the claims hereinafter and their equivalents; in the claims, all of the terms should be understood, unless indicated otherwise, within their broadest possible meaning.

The invention claimed is:

1. A compound of formula (IIIa):

(IIIa)

in which
u is an integer between 1 and 5;
$R^7$, $R^8$, $R^9$ and $R^{10}$ represent a hydrogen,
$R^1$, $R^5$, and $R^6$ independently of one another and, for $R^1$, independently for each of the units $(CHR^1)_u$ represent a group of formula (II), the group of formula (II) being (II)

and comprising at least 4 carbon atoms and at most 80 carbon atoms, and in which n is an integer between 1 and 10;
in which A is selected, independently for each of the units $(A)_n$, from the groups of formula (IIa), (IIb), or (IIc)

—[(CH$_2$)$_q$—CH=CH—(CH$_2$)$_t$]— (IIa),

—[(CH$_2$)$_v$—CH(CH$_2$NR$^3$R$^4$)—CH$_2$—(CH$_2$)$_w$]— (IIb),

—[(CH$_2$)$_y$—CH(CH$_2$OH)—CH$_2$—(CH$_2$)$_z$]— (IIc),

—[(CH$_2$)$_x$]— (IId), where q, t, v, w, y and z are integers between 0 and 20, the sum of q+t, v+w or y+z being less than 20;
x is an integer between 10 and 30;
$R^3$ and $R^4$ independently of one another represent H, $C_1$-$C_{10}$ alkyl, $C_6$-$C_{12}$ aryl, benzyl, $C_3$-$C_{10}$ cycloalkyl, or $R^3$ and $R^4$ together with the nitrogen atom to which they are attached form a five- or six-membered heterocycle;
the compound of formula (IIIa) comprising at least one group of formula (II) in which at least one of the units $(A)_n$ is of formula (IIb), and at least one group of formula (II) in which at least one of the units $(A)_n$ of formula (IIc).

2. A compound of formula (IIIa):

(IIIa)

in which
$R^7$, $R^8$, $R^9$, and $R^{10}$ represent a hydrogen,
u is 1,
$R^1$, $R^5$, and $R^6$ independently of one another represent a group of formula (II), the group of formula (II) being (II)

and comprising at least 4 carbon atoms and at most 80 carbon atoms, and in which n is an integer between 1 and 10;
in which A is selected, independently for each of the units $(A)_n$, from the groups of formula (IIb) or (IIc)

—[(CH$_2$)$_q$—CH=CH—(CH$_2$)$_t$]— (IIa),

—[(CH$_2$)$_v$—CH(CH$_2$NR$^3$R$^4$)—CH$_2$—(CH$_2$)$_w$]— (IIb),

—[(CH$_2$)$_y$—CH(CH$_2$OH)—CH$_2$—(CH$_2$)$_z$]— (IIc),

—[(CH$_2$)$_x$]— (IId), where q, t, v, w, y and z are integers between 0 and 20, the sum of q+t, v+w or y+z being less than 20;
x is an integer between 10 and 30;
$R^3$ and $R^4$ independently of one another represent H, $C_1$-$C_{10}$ alkyl, $C_6$-$C_{12}$ aryl, benzyl, $C_3$-$C_{10}$ cycloalkyl, or $R^3$ and $R^4$ together with the nitrogen atom to which they are attached form a five- or six-membered heterocycle;
n is an integer between 1 and 5;
each of the substituents $R^1$, $R^5$, and $R^6$ comprising at least 12 carbon atoms and at most 25 carbon atoms,
the compound of formula (IIIa) comprising at least one group of formula (II) in which at least one of the units $(A)_n$ is of formula (IIb), and at least one group of formula (II) in which at least one of the units $(A)_n$ is of formula (IIc).

3. The compound as claimed in claim 1 of formula (IIIa) in which
$R^7$, $R^8$, $R^9$, and $R^{10}$ represent a hydrogen and u is 1,
$R^1$, $R^5$, and $R^6$ independently of one another represent a group of formula (II) in which n is 1,
A is a group of formula (IIb) or (IIc)

[(CH$_2$)$_v$—CH(CH$_2$NR$^3$R$^4$)—CH$_2$—(CH$_2$)$_w$]— (IIb), or

[(CH$_2$)$_y$—CH(CH$_2$OH)—CH$_2$—(CH$_2$)$_z$]— (IIc);

$R^3$ and $R^4$ independently of one another represent H, $C_1$-$C_{10}$ alkyl, $C_6$-$C_{12}$ aryl, benzyl, $C_3$-$C_{10}$ cycloalkyl, or $R^3$ and $R^4$ together with the nitrogen atom to which they are attached form a five- or six-membered heterocycle;
v, y, w, and z independently of one another are an integer between 4 and 9, where v+w or y+z is an integer between 11 and 15,
the compound of formula (IIIa) comprising at least one group of formula (II) in which A is of formula (IIb) and at least one group of formula (II) in which A is of formula (IIc).

4. The compound as claimed in claim 1 where $R^3$ and $R^4$ independently represent $C_2$-$C_8$ alkyl.

5. The compound as claimed in claim 1 where n is 1 in the group of formula (II), and the compound (IIIa) comprises at least one group of formula (II) in which A is (IIb), and at least one group of formula (II) in which A is (IIc).

6. The compound as claimed in claim 2 of formula (IIIa) in which $R^7$, $R^8$, $R^9$, and $R^{10}$ represent a hydrogen and u is 1, $R^1$, $R^5$, and $R^6$ independently of one another represent a group of formula (II) in which n is 1, A is a group of formula (IIb) or (IIc)

$$[(CH_2)_v\text{—}CH(CH_2NR^3R^4)\text{—}CH_2\text{—}(CH_2)_w]\text{—} \quad \text{(IIb), or}$$

$$[(CH_2)_y\text{—}CH(CH_2OH)\text{—}CH_2\text{—}(CH_2)_z]\text{—} \quad \text{(IIc);}$$

$R^3$ and $R^4$ independently of one another represent H, $C_1$-$C_{10}$ alkyl, $C_6$-$C_{12}$ aryl, benzyl, $C_3$-$C_{10}$ cycloalkyl, or $R^3$ and $R^4$ together with the nitrogen atom to which they are attached form a five- or six-membered heterocycle;

v, y, w, and z independently of one another are an integer between 4 and 9, where v+w or y+z is an integer between 11 and 15, the compound of formula (IIIa) comprising at least one group of formula (II) in which A is of formula (IIb) and at least one group of formula (II) in which A is of formula (IIc).

7. The compound as claimed in claim 2 where $R^3$ and $R^4$ independently represent $C_2$-$C_8$ alkyl.

8. The compound as claimed in claim 2 where n is 1 in the group of formula (II), and the compound (IIIa) comprises at least one group of formula (II) in which A is (IIb), and at least one group of formula (II) in which A is (IIc).

\* \* \* \* \*